(12) United States Patent
Moore et al.

(10) Patent No.: US 11,707,258 B2
(45) Date of Patent: Jul. 25, 2023

(54) DEVICE AND METHOD FOR INTRAVASCULAR IMAGING AND SENSING

(71) Applicant: ZED MEDICAL, INC., Livermore, CA (US)

(72) Inventors: Thomas C. Moore, Livermore, CA (US); Kendall R. Waters, Sammamish, WA (US); Robert Zelenka, Milpitas, CA (US)

(73) Assignee: Zed Medical, Inc., Livermore, CA (US)

( * ) Notice: Subject to any disclaimer, the term of this patent is extended or adjusted under 35 U.S.C. 154(b) by 0 days.

(21) Appl. No.: 17/333,361

(22) Filed: May 28, 2021

(65) Prior Publication Data
US 2022/0133268 A1    May 5, 2022

Related U.S. Application Data

(63) Continuation of application No. 15/796,760, filed on Oct. 28, 2017, now abandoned.
(Continued)

(51) Int. Cl.
*A61B 8/00* (2006.01)
*A61B 5/02* (2006.01)
(Continued)

(52) U.S. Cl.
CPC .......... *A61B 8/445* (2013.01); *A61B 5/02007* (2013.01); *A61B 5/0215* (2013.01);
(Continued)

(58) Field of Classification Search
CPC ... A61B 8/445; A61B 5/02007; A61B 5/0215; A61B 8/06; A61B 5/026; A61B 8/04;
(Continued)

(56) References Cited

U.S. PATENT DOCUMENTS 4,917,097 A    4/1990  Proudian et al.
5,357,979 A *  10/1994 Imran ............... A61M 25/0158
                                                    604/95.05
(Continued)

FOREIGN PATENT DOCUMENTS

WO    2015/073817 A1    5/2015

OTHER PUBLICATIONS

Patent Cooperation Treaty International Searching Authority, International Search Report and Written Opinion for PCT/US17/58911 dated Jan. 30, 2018, 13 pages.
(Continued)

*Primary Examiner* — Yi-Shan Yang
*Assistant Examiner* — Alexei Bykhovski
(74) *Attorney, Agent, or Firm* — Merchant & Gould, P.C.

(57) ABSTRACT

An intravascular sensor device can be used to guide treatment of a diseased blood vessel in the body of a patient. In some examples, the intravascular sensor device includes a pressure sensor and an ultrasound transducer. The intravascular sensor device is used to measure a pressure within the diseased blood vessel and acquire an ultrasound image of the diseased blood vessel. The pressure may be measured during hyperemic blood flow that is caused by a pharmacologic vasodilator drug. The measured pressure can be used to calculate a fractional flow reserve value. The ultrasound image can be used to determine a physical dimension of the blood vessel, such as cross-sectional area. The fractional flow reserve value and physical dimensions of the blood vessel can be used to optimize patient treatment.

16 Claims, 16 Drawing Sheets

Related U.S. Application Data

(60) Provisional application No. 62/449,604, filed on Jan. 24, 2017, provisional application No. 62/413,987, filed on Oct. 28, 2016.

(51) Int. Cl.
*A61B 5/0215* (2006.01)
*A61B 8/06* (2006.01)
*A61B 8/04* (2006.01)
*A61B 5/026* (2006.01)

(52) U.S. Cl.
CPC .............. *A61B 8/06* (2013.01); *A61B 5/026* (2013.01); *A61B 8/04* (2013.01); *A61B 8/4461* (2013.01)

(58) Field of Classification Search
CPC ... A61B 8/4461; A61B 8/0841; A61B 8/0891; A61B 8/12; A61B 8/4416; A61B 8/4483; A61B 8/5223; A61B 2562/166; A61B 2576/023; A61B 5/02158; A61B 2505/05; A61B 2562/0247; A61B 2562/04; A61B 2562/164; A61B 2562/22; G16H 30/40
See application file for complete search history.

(56) References Cited

U.S. PATENT DOCUMENTS

| | | | |
|---|---|---|---|
| 5,554,119 A * | 9/1996 | Harrison | A61M 25/1002 604/101.05 |
| 6,129,672 A | 10/2000 | Seward et al. | |
| 6,471,656 B1 | 10/2002 | Shalman et al. | |
| 2004/0092830 A1 | 5/2004 | Scott et al. | |
| 2005/0054905 A1 * | 3/2005 | Corl | A61B 5/14539 600/309 |
| 2005/0121734 A1 * | 6/2005 | Degertekin | B06B 1/0292 438/48 |
| 2009/0163818 A1 * | 6/2009 | Zelenka | A61M 25/0054 600/467 |
| 2009/0318003 A1 * | 12/2009 | Hossack | A61B 8/12 439/299 |
| 2010/0286522 A1 | 11/2010 | Beach et al. | |
| 2011/0092955 A1 | 4/2011 | Purdy et al. | |
| 2013/0237864 A1 | 9/2013 | Mazar et al. | |
| 2013/0303914 A1 | 11/2013 | Hiltner et al. | |
| 2014/0005558 A1 | 1/2014 | Gregorich | |
| 2014/0180122 A1 | 6/2014 | Stigall et al. | |
| 2014/0180127 A1 | 6/2014 | Meyer et al. | |
| 2014/0276011 A1 | 9/2014 | Schmitt et al. | |
| 2015/0038949 A1 * | 2/2015 | Singh | A61B 5/6849 604/891.1 |
| 2015/0112188 A1 | 4/2015 | Stigall et al. | |
| 2015/0133800 A1 * | 5/2015 | McCaffrey | A61M 25/007 600/486 |
| 2015/0133892 A1 | 5/2015 | Joe et al. | |
| 2015/0223707 A1 | 8/2015 | Ludoph | |
| 2015/0273184 A1 * | 10/2015 | Scott | H01B 7/04 29/842 |
| 2015/0305708 A1 * | 10/2015 | Stigall | A61B 8/12 600/467 |
| 2016/0067456 A1 * | 3/2016 | Burkett | A61B 5/0215 600/486 |
| 2016/0081657 A1 | 3/2016 | Rice | |
| 2016/0166232 A1 | 6/2016 | Merritt | |
| 2017/0032523 A1 | 2/2017 | Klaiman et al. | |
| 2017/0055941 A1 | 3/2017 | Stigall et al. | |
| 2017/0348509 A1 * | 12/2017 | Burkholz | A61M 25/0127 |
| 2019/0069949 A1 * | 3/2019 | Vrba | A61B 17/122 |

OTHER PUBLICATIONS

Extended European Search Report for Application No. 17864213.8 dated Jul. 16, 2020.

* cited by examiner

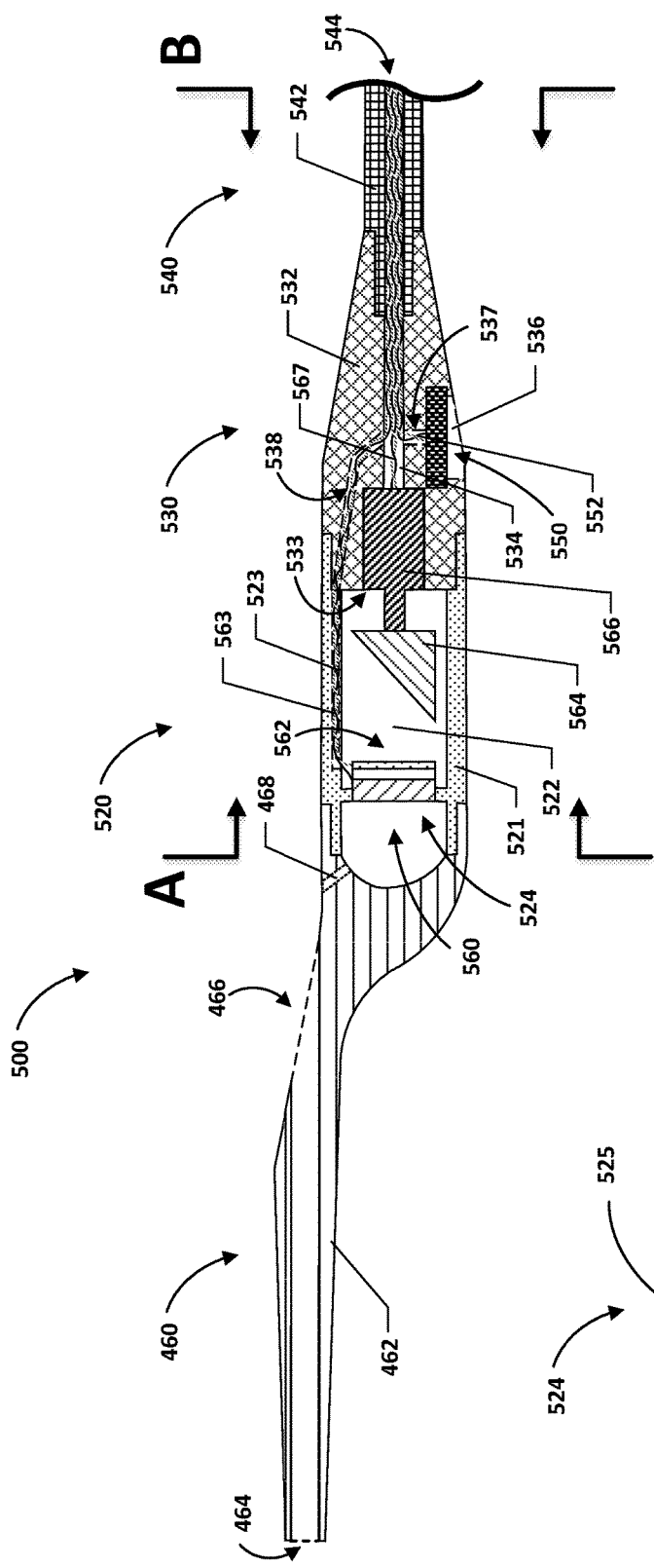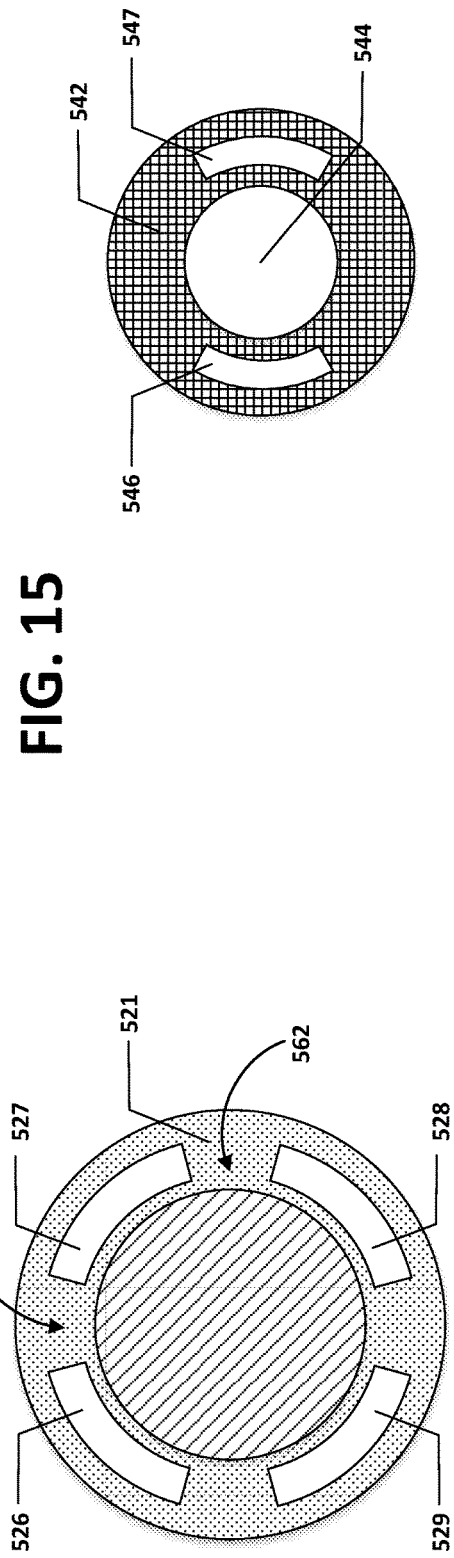
FIG. 15
FIG. 15A
FIG. 15B

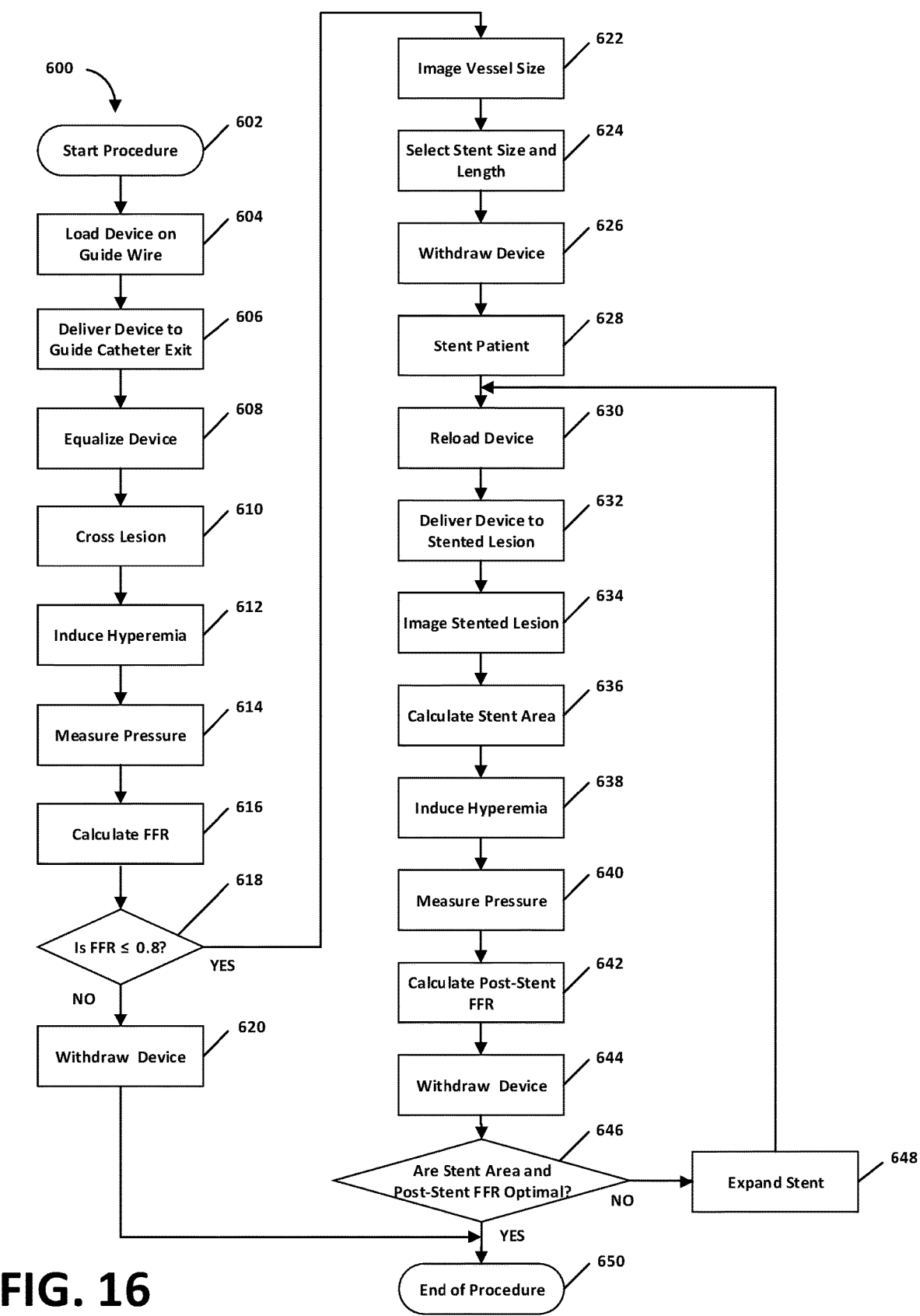

DEVICE AND METHOD FOR INTRAVASCULAR IMAGING AND SENSING

FIELD

The present application relates generally to medical devices used for imaging and sensing of blood vessels. The application further relates to catheters used for ultrasound imaging and pressure sensing within blood vessels.

BACKGROUND

Diagnostic imaging and sensing provides critical information to guide catheter-based interventions for blood vessels. A common type of diagnostic sensing device is a pressure-sensing guide wire or catheter. A pressure-sensing guide wire or catheter is typically used to determine physiological details of a diseased blood vessel, such as whether an atherosclerotic lesion induces ischemia in a patient. Physicians will generally treat ischemia-inducing lesions with a stent.

Another common type of diagnostic imaging device is an intravascular ultrasound (IVUS) imaging catheter. An IVUS imaging catheter is often delivered to a region of interest within a stented blood vessel in order to determine structural details, such as stent area. If the stent is determined to be underexpanded the physician will often post-dilate the stent with a balloon catheter.

A challenge to the use of both pressure-sensing devices and IVUS catheters in a patient is the current limitation that two separate devices are required. The use of two separate diagnostic devices can complicate clinical workflow. The use of two separate diagnostic devices will also generally increase the cost of the procedure.

A challenge to combining IVUS imaging and pressure sensing capabilities into a single medical device is limiting the device size so that device size does not substantially influence blood flow in a vessel. The size of currently available IVUS catheters is known to substantially influence blood flow in a vessel.

It would be advantageous to have a single medical device that enabled both pressure sensing and ultrasound imaging of blood vessels. It would also be advantageous to have a medical device whose influence on blood flow in a blood vessel was minimal.

BRIEF DESCRIPTION OF THE DRAWINGS

The foregoing aspects and many of the attendant advantages of the claims will become more readily appreciated as the aspects and advantages of the claims become better understood by reference to the following detailed description, when taken in conjunction with the accompanying drawings, wherein:

FIG. 15 is a partial sectional view of a catheter in accordance with an embodiment of the invention;

FIG. 15A is a sectional view taken along lines A-A of FIG. 15;

FIG. 15B is a sectional view taken along lines B-B of FIGS. 15; and

FIG. 16 is a flow diagram illustrating exemplary processing stages for guidance of a stenting procedure in accordance with an embodiment of the invention.

DETAILED DESCRIPTION

Summary

Figure 1:
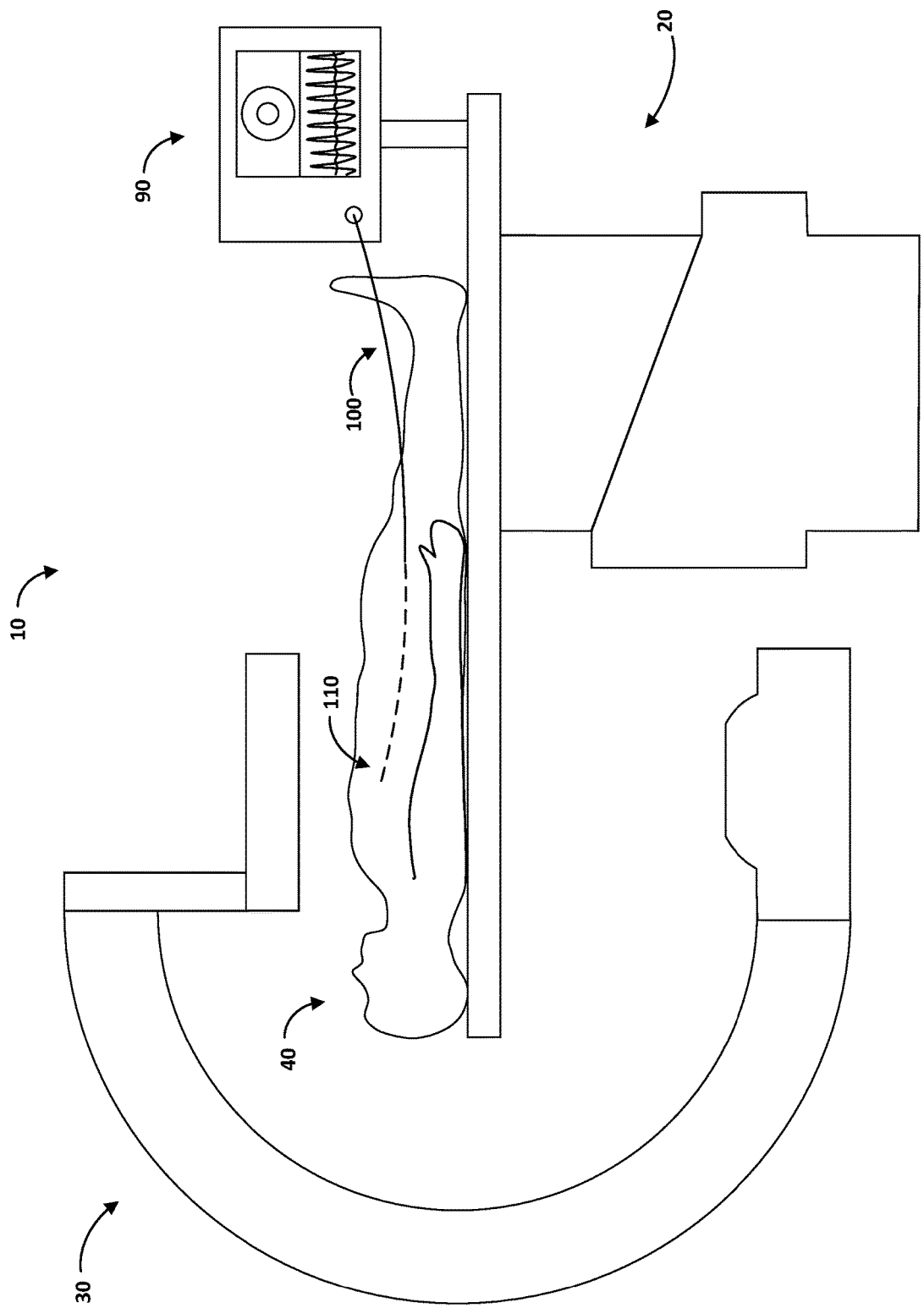
FIG. 1 is a side view of a catheter laboratory.

In accordance with one embodiment, a sensing catheter is deployed in a percutaneous coronary intervention configuration in a blood vessel, the sensing catheter having a distal-end first portion having a first cross-sectional area. The first portion may include an ultrasound transducer array, a pressure sensor, and a guide wire lumen, the first portion being deployed within a first length of the blood vessel. A second portion of the sensing catheter may be of a second reduced cross-sectional area, the second portion being deployed within a second length of blood vessel, the reduced cross-sectional area reducing an influence of the catheter on a pressure reading of the pressure sensor and enabling a more indicative pressure reading of the pressure sensor than if the diameter of the second section were not reduced. The second portion may be proximal to the first portion.

In another embodiment, a sensing catheter for insertion into a blood vessel includes a distal-end first portion having a first cross-sectional area. The first portion may include an ultrasound transducer array, a pressure sensor, and a lumen for receiving a guide wire. A second portion of the sensing catheter may be of a second reduced cross-sectional area, wherein the reduced diameter of the second portion reduces an influence of the catheter on a pressure reading of the pressure sensor and enables a more indicative pressure reading of the pressure sensor than if the diameter of the second portion were not reduced. The second portion may be proximal to the first portion. The guide wire lumen may be discontinued along a length of the second portion. The pressure sensor may be a piezoresistive pressure sensor, an optical pressure sensor, etc. The ultrasound transducer array may be configured to operate at least one frequency between 20 MHz and 80 MHz. The ultrasound transducer array may include at least one capacitive micromachined ultrasound transducer, at least one piezoelectric micromachined ultrasound transducer, etc. The pressure sensor and the ultrasound transducer array may be fabricated on the same substrate, which may include complementary metal-oxide-semiconductor circuitry.

The second portion of the sensing catheter may include a first section that is substantially tubular and has an outer diameter of 0.03 inches or smaller, and a second section that is substantially tubular and has an outer diameter between 0.016 inches and 0.064 inches, inclusive. The second portion may include include a first end and a second end wherein the flexibility of the first section varies between the first end and the second end.

A communication assembly may be configured to receive signals from the pressure sensor, send signals to the ultrasound transducer assembly, and receive signals from the ultrasound transducer assembly. It may include a flexible circuit assembly and may also include at least one cable, at least one optical fiber, etc.

In accordance with another embodiment, an intravascular device includes an elongated body including a first portion having a first cross-sectional area and a lumen configured to receive a guide wire; a second portion bonded to the first portion having a second cross-sectional area less than the first cross-sectional area; a first sensor adapted to measure pressure; a second sensor configured to transmit and receive ultrasound pressure; and a communication assembly adapted to receive signals from the first sensor, send signals to the second sensor, and receive signals from the second sensor.

In another embodiment, a method of determining a condition of a blood vessel uses a guide wire and a catheter including an ultrasound transducer array and a pressure sensor. Steps include, with a single insertion of the catheter, performing at least one pressure measurement, and imaging an area of interest of the blood vessel. During the pressure measurement, a reduced cross-sectional area along a portion of the catheter reduces an influence of the catheter on the pressure measurement, enabling a more indicative pressure measurement. Pressure measurement may be performed during a hyperemic blood flow rate caused by a pharmacologic vasodilator drug. Using a processor, a fractional flow reserve value may be determined based on the at least one pressure measurement during hyperemic blood flow. The blood vessel may include a lesion. A processor may be used to further determine a physical dimension of the blood vessel, wherein the physical dimension is one of a cross-sectional area of the blood vessel, a diameter of the blood vessel, and a length of the blood vessel.

In accordance with another embodiment, a method is provided of evaluating a stent within a blood vessel, using a guide wire and a catheter including an ultrasound transducer array and a pressure sensor. Steps include, with a single insertion of the catheter, performing a pressure measurement, and imaging an area of the blood vessel including the stent. During the measurement of pressure, a reduced cross-sectional area along a portion of the catheter reduces an influence of the catheter on the pressure measurement, enabling a more indicative pressure measurement. The at least one pressure measurement may be performed during a hyperemic blood flow rate caused by a pharmacologic vasodilator drug. A processor may be used to determine a fractional flow reserve value based on the at least one pressure measurement during hyperemic blood flow. A processor may be used to further determine a physical dimension of the stent wherein the physical dimension is one of a cross-sectional area of the stent, a diameter of the stent, and maximum distance between stent and blood vessel wall.

In accordance with another embodiment, a method includes inserting an intravascular sensing device into a body of a patient, controlling the intravascular sensing device to acquire at least one pressure measurement within a blood vessel, and controlling the intravascular sensing device to acquire at least one ultrasound image within the blood vessel. The blood vessel may comprise at least one of a lesion and stent. The at least one pressure measurement may be performed during a hyperemic blood flow rate caused by a pharmacologic vasodilator drug. A processor may be used to determine a fractional flow reserve value based on the at least one pressure measurement during hyperemic blood flow. A processor may be used to further determine a physical dimension of the blood vessel wherein the physical dimension is one of a cross-sectional area of the blood vessel, a diameter of the blood vessel, and a length of the blood vessel.

Description

The following discussion is presented to enable a person skilled in the art to make and use the subject matter disclosed herein. The general principles described herein may be applied to embodiments and applications other than those detailed above without departing from the spirit and scope of the present detailed description. The present disclosure is not intended to be limited to the embodiments shown, but is to be accorded the widest scope consistent with the principles and features disclosed or suggested herein.

This application provides embodiments of pressure-sensing and IVUS imaging catheter for use in guiding treatment of patients with atherosclerotic disease. In some cases, the catheter is designed for use in a coronary artery. In further cases, the catheter is designed for use in peripheral arteries. Skilled artisans will understand that this application is not limited to the above-referenced arteries.

FIG. 1 is an illustrative example of a catheter laboratory 10 that includes a patient table 20 and an X-ray C-arm 30 for guiding diagnostic and therapeutic cardiovascular interventions of a patient 40. The laboratory 10 may also include a pressure sensing and IVUS imaging console 90 and catheter 100. Console 90 may house various operating components that control the operation of the catheter 100, send signals to or receive signals from catheter, or store data generated by or used with the catheter. In some examples, console 90 also includes a user interface that enables a physician to interact with the catheter 100 and display information generated by the catheter. The broken lines in FIG. 1 represent portions of catheter 100 within the patient 40.

Figure 2:
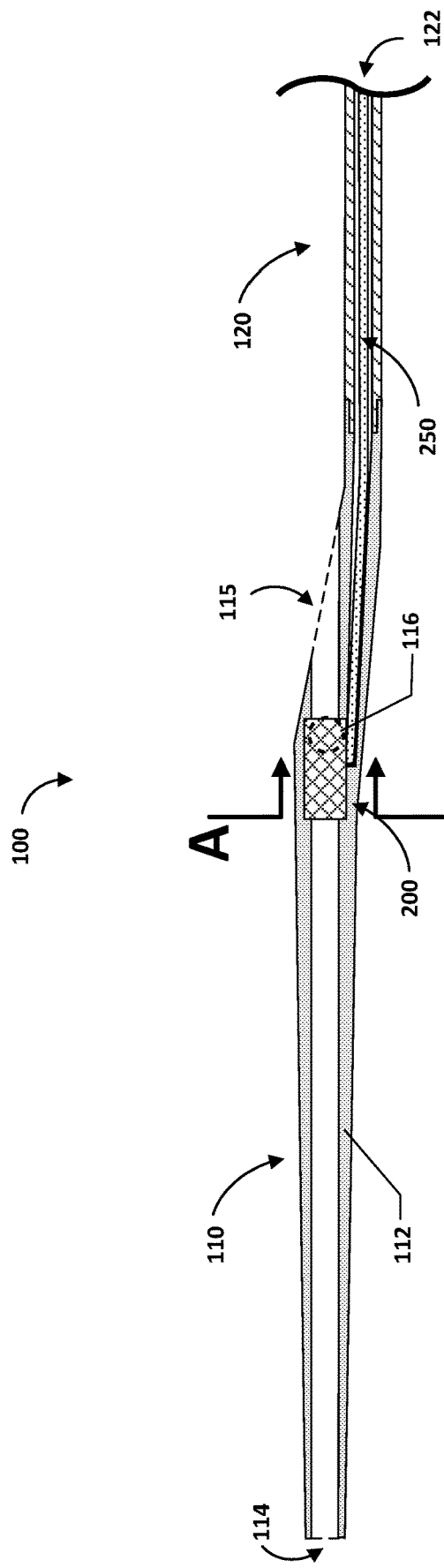
FIG. 2 is a partial sectional side view of a catheter in accordance with an embodiment of the invention.

Referring to FIG. 2, a partial sectional view of the distal end of an IVUS imaging and pressure sensing catheter 100 according to one embodiment of the invention is shown. For illustrative purposes only, embodiments of the invention described herein are appropriate for intracoronary catheters. The described embodiments do not limit application of the invention to only intracoronary catheters. In the embodiment shown, the catheter 100 includes a distal tip 110, a distal shaft 120, and a sensor assembly 200. The distal tip 110 may include a tapered, elongated tube 112 having at least one layer. The distal tip 110 further includes a guide wire lumen entry port 114, a guide wire lumen exit port 115, and a side port 116. The distal tip has an inner diameter suitable for an 0.014" guide wire, generally an inner diameter of 0.0165". The distal tip wall may taper from a proximal thickness between 0.003" and 0.009" to a distal thickness between 0.001" and 0.003". The distal tip has a length suitable for tracking along the guide wire, generally a length between 5 mm and 30 mm. Pebax has been found to be a suitable material for the distal tip 110. A distal tip may also include an inner liner made of high-density polyethylene (HDPE) or polytetrafluoroethylene (PTFE) to reduce friction between the distal tip and a guide wire (not shown). The side port 116 enables fluid communication between a blood-filled coronary artery and at least a portion of the sensor assembly 200. A platinum/iridium radiopaque marker band (not shown) may be included in the distal tip to aid visualization of the catheter in x-ray angiographic images.

The distal tip 110 is bonded to the distal shaft 120. The distal shaft 120 can have a proximal end, a distal end, and a length extending between the proximal and distal ends.

The distal shaft can include any suitable material capable of having different flexural moduli along the shaft's length. In some embodiments, the distal shaft includes a hypotube. The hypotube may be a spiral-cut, stainless steel hypotube.

In general, a varying flexural modulus of the catheter, decreasing toward the distal end, may be achieved in a variety of ways. One way is to use different elastomers along the length of the catheter. Another is to vary the wall thickness of the catheter along its length. Another is to form scores or perforations of varying density along the length of the catheter (which may employ an elastomeric tube, a metal tube, or some combination thereof). These various methods may also be combined to achieve the desired change in flexural modulus along the length of the catheter.

Referring still to FIG. 2, the distal shaft further includes at least one lumen 122. The distal shaft may further include a polymer jacket and a liner to seal the lumen 122 from the external blood-filled coronary artery. The distal shaft 120 should have an outer diameter sufficiently small to minimize effects on coronary artery blood flow. The outer diameter of the distal shaft 120 is preferably 0.018" or smaller. The inner diameter of the distal shaft may be 0.016" or smaller.

The distal tip 110, in which an imaging sensor is housed, may be of larger diameter relative to the distal shaft 120. This larger diameter allows for a larger diameter imaging sensor that provides a higher quality image.

The present catheter may be configured in a "long rail" or "long engagement" configuration or a "short rail" or "short engagement" configuration, in accordance with the length and extent of a guide wire lumen. The catheter of FIG. 2 is exemplary of a short engagement configuration.

In one scenario, the short engagement configuration may be deployed across a lesion such that, distal of the lesion, a guide wire is enclosed within the guide wire lumen of the catheter. Within the lesion, the guide wire may be unenclosed, having exited the guide wire lumen through an exit port. Furthermore, the diameter (or, more generally, cross-sectional area) of the portion of the catheter within the lesion may be reduced. The combined diameters of the reduced catheter portion and the guide wire is preferably below a threshold above which interference with a pressure reading by a pressure sensor distal of the lesion is likely. This threshold is dependent on the typical size of the artery and the degree of occlusion. In coronary applications, it may be determined in accordance with an average adult artery lumen cross-sectional area and in accordance with an assumed percentage of occlusion.

The short engagement configuration has the further advantage that the catheter and the unenclosed guide wire tend to hug the artery wall, side by side, in such a way that protrusion into the artery is lessened. This reduced protrusion further reduces interference with pressure measurement.

Figure 2A:
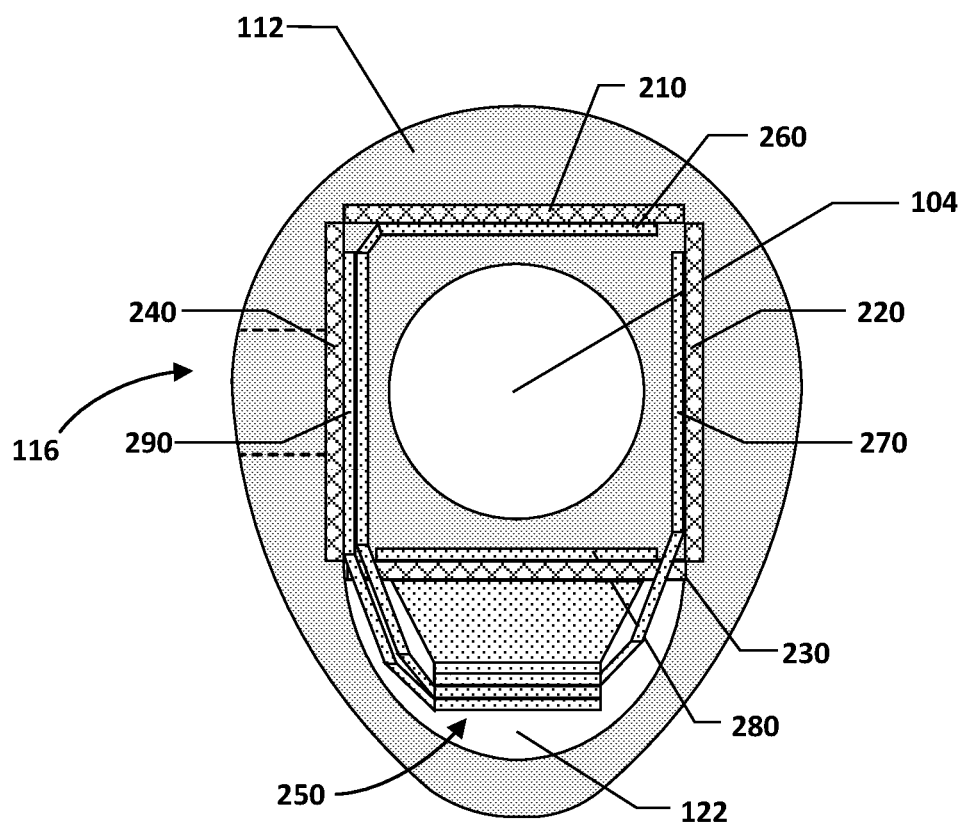
FIG. 2A is a sectional view taken along lines A-A of FIG. 2.

Referring to FIGS. 2 and 2A, the sensor assembly 200 according to one embodiment of the invention includes a set of four sensor subassemblies 210, 220, 230, 240 and a flexible circuit assembly 250. The flexible circuit assembly further includes four flexible circuit arms 260, 270, 280, 290. The four sensor subassemblies and the distal sections of the four flexible circuit arms are located within the distal tip 110. The proximal section of the flexible circuit assembly 250 is located in the lumen 122 of the distal tip 110 and distal shaft 120. Each sensor subassembly is electrically connected to one flexible circuit arm. Sensor subassembly 210 and flexible circuit arm 260, sensor subassembly 220 and flexible circuit arm 270, sensor subassembly 230 and flexible circuit arm 280, and sensor subassembly 240 and flexible circuit arm 290 are respectively electrically connected. In another embodiment, the sensor assembly may include discrete conductive wires. In still another embodiment, the sensor assembly may include discrete conductive wires in combination with a flexible circuit assembly. In yet still another embodiment, the sensor assembly may include at least one fiber optic cable.

Figure 3:
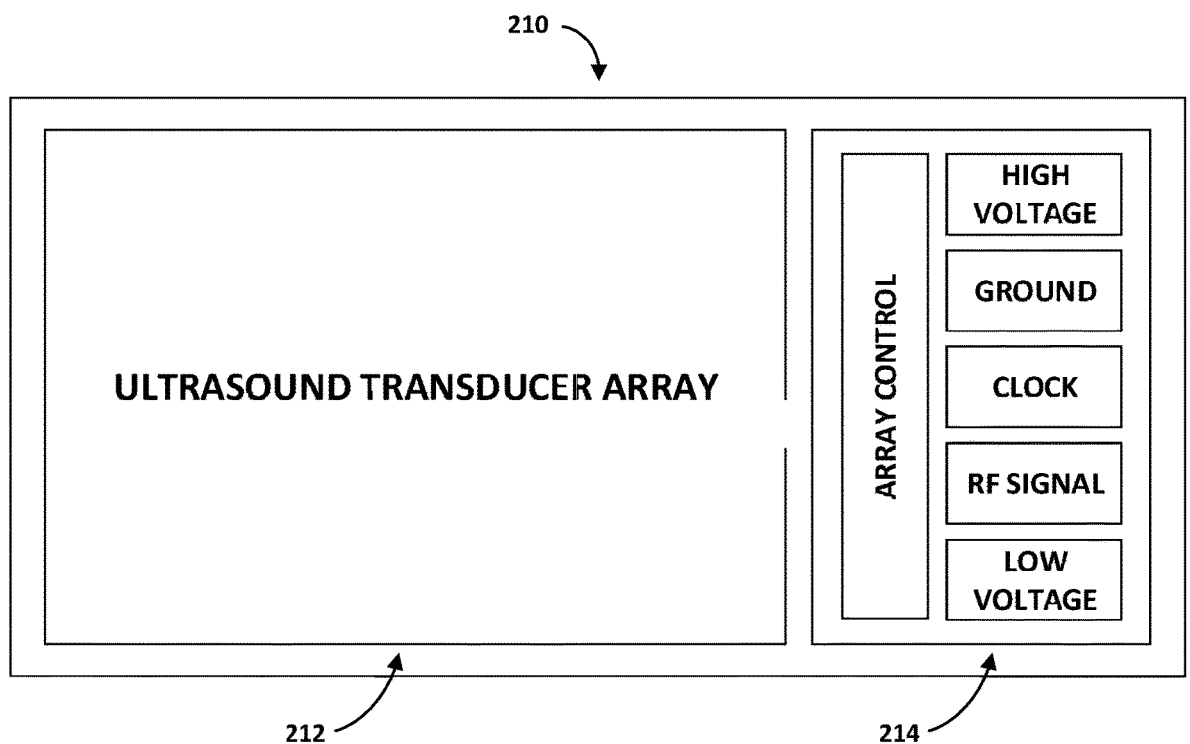
FIG. 3 is a block diagram of an ultrasound imaging array in accordance with an embodiment of the invention.
Figure 3A:
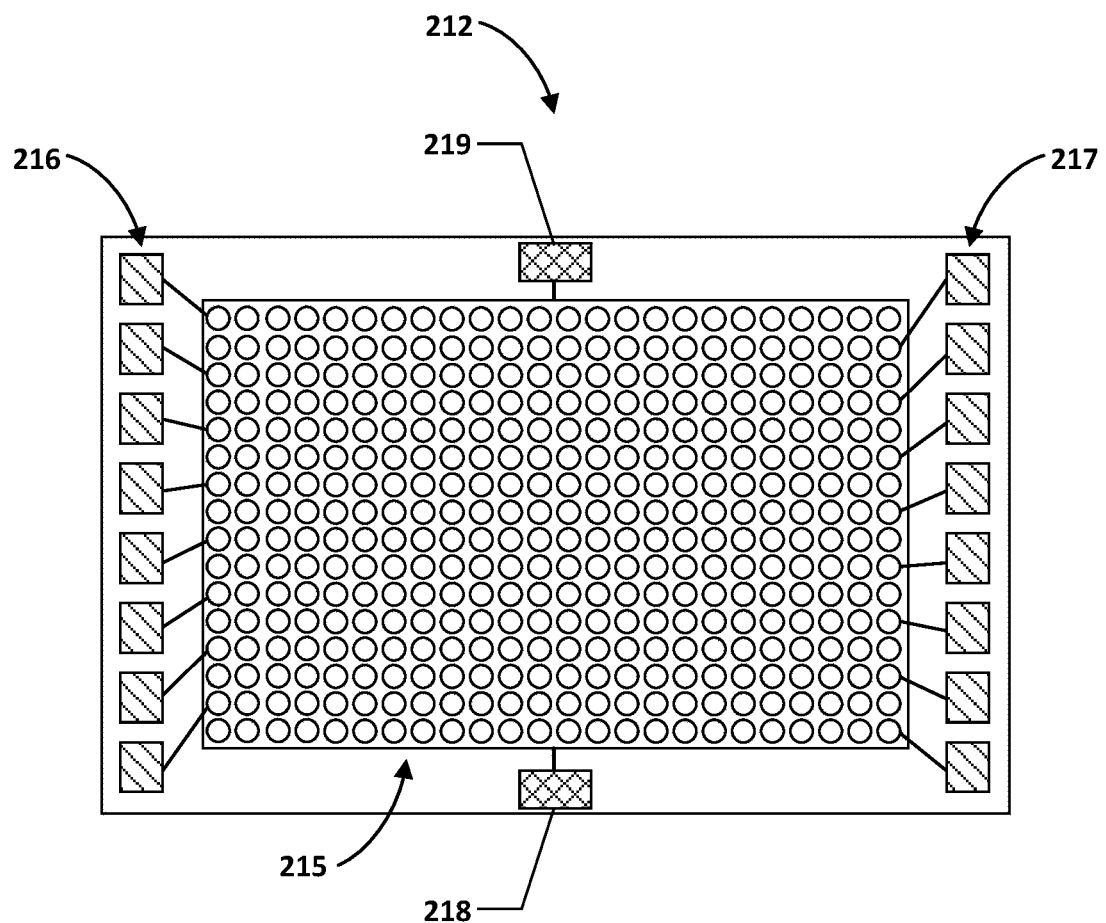
FIG. 3A is a top view of an ultrasound imaging array in accordance with an embodiment of the invention.

Referring to FIGS. 3 and 3A, the sensor subassembly 210 according to one embodiment of the invention includes an ultrasound transducer array 212 and sensor control circuitry 214. The sensor subassembly 210 may include capacitive micromachined ultrasound transducers (CMUTs) on complementary metal-oxide-semiconductor (CMOS), or CMUT-on-CMOS.

The ultrasound transducer array 212 includes an array of CMUT membranes 215, array row pads 216, 217, and ground pads 218, 219. The width of the ultrasound transducer array 212 may be between 0.30 mm and 0.60 mm. The size of a 0.014" guide wire (or approx. 0.35 mm) and the outer diameter of the distal tip 110 can be used to respectively set a minimum and a maximum of the array width. The length of the ultrasound array 212 may be between 0.5 mm and 2 mm. Selection of the length of the ultrasound array will be a trade-off between deliverability and pressure sensitivity, wherein a shorter array may provide better deliverability and a longer array may provide better pressure sensitivity or other imaging characteristics. The CMUT membranes may operate at frequencies common for IVUS catheters, typically between 10 MHz and 80 MHz. The size and pitch of the CMUT membranes can be selected to optimize imaging performance. According to one embodiment of the invention a 30 MHz array may have a CMUT membrane size and pitch of respectively 0.020 mm and 0.025 mm. For an array size of 16×24 elements the array size is approximately 0.4 mm by 0.6 mm. In another embodiment, the array size is 24×32 elements with dimensions of approximately 0.6 mm by 0.8 mm.

The sensor control circuitry 214 enables control of the ultrasound transducer array 212, including high-voltage bias excitation of the CMUT membranes, control of the transmit and receive sequences, and communication with the console 90 via the flexible circuit arm 260. The sensor subassemblies 220, 230 have the same design as the sensor subassembly 210.

Figure 4:
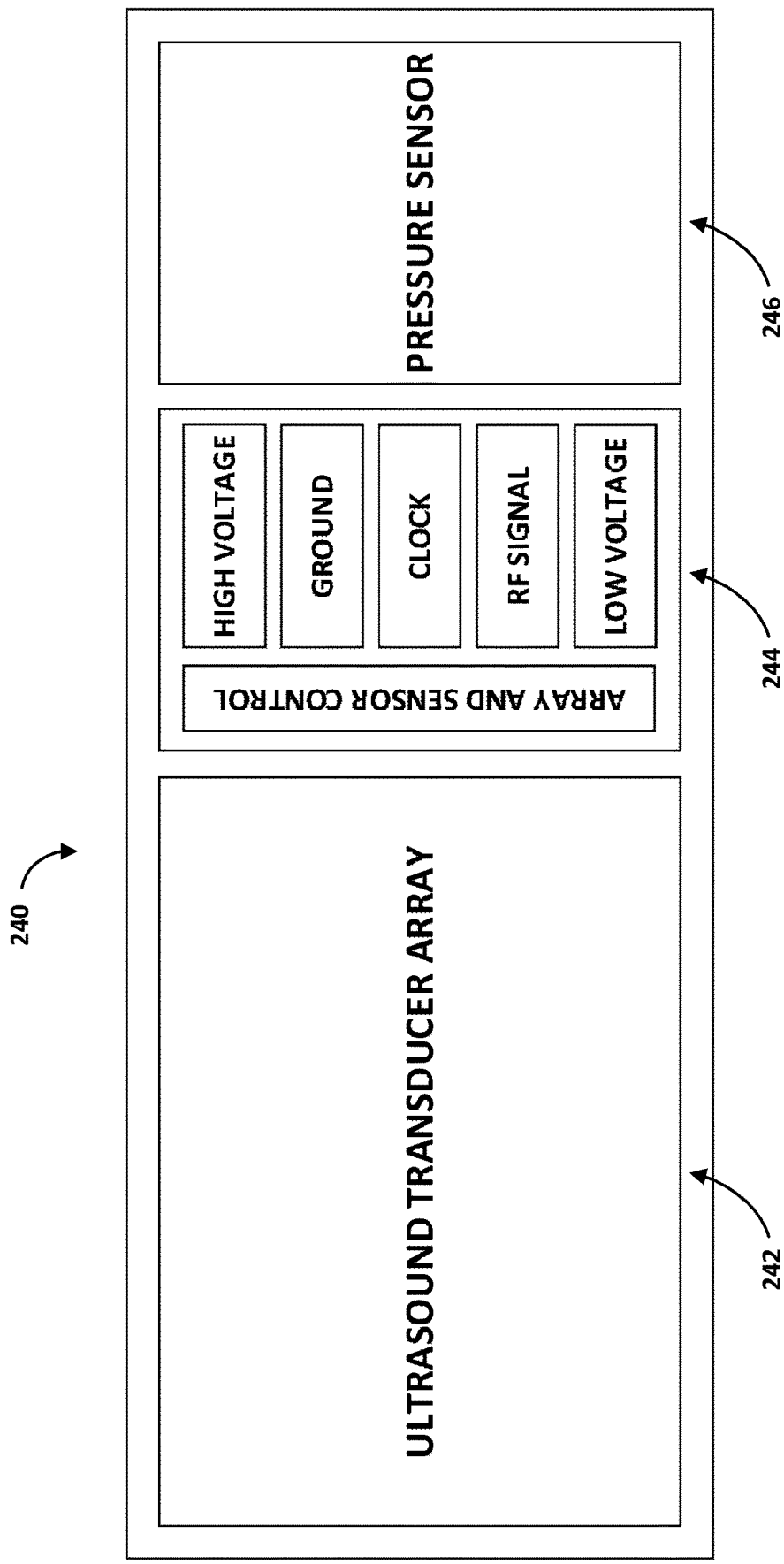
FIG. 4 is a block diagram of a combined ultrasound imaging array and pressure sensor in accordance with an embodiment of the invention.
Figure 4A:
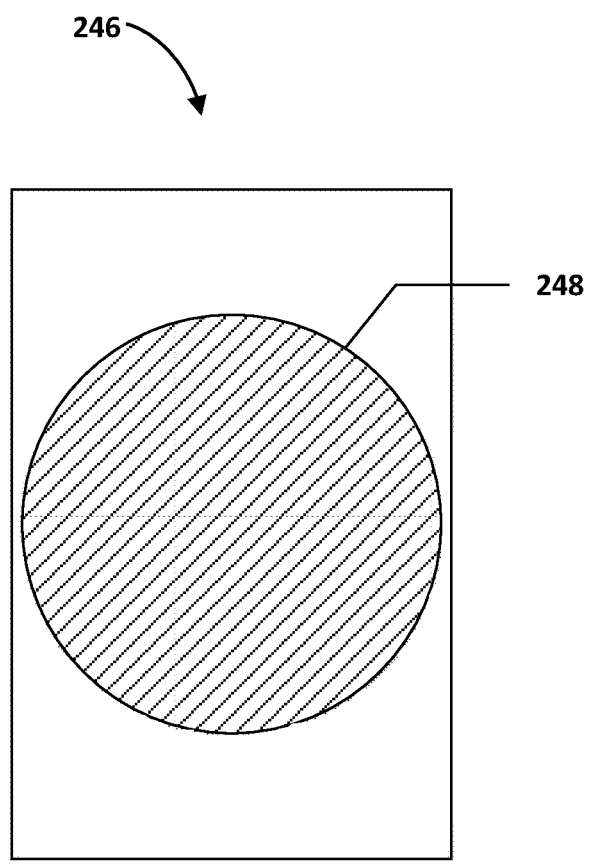
FIG. 4A is a top view of a pressure sensor in accordance with an embodiment of the invention.

Referring to FIGS. 4 and 4A, the sensor subassembly 240 according to one embodiment of the invention includes an ultrasound transducer array 242, sensor control circuitry 244, and a pressure sensor 246. The sensor subassembly 240 may include CMUT-on-CMOS. The ultrasound transducer array 242 may have the same design as the ultrasound transducer array 212.

The sensor control circuitry 244 enables control of the ultrasound transducer array 242 and the pressure sensor 246, including high-voltage bias and excitation of the CMUT membranes, control of the transmit and receive sequences of the ultrasound transducers, pressure sensor reading, and communication with the console 90 via the flexible circuit arm 290. The pressure sensor 246 may include a piezoresistive sensor 248. The size of the pressure sensor may be between 0.35 mm and 0.5 mm, similar to the width of the ultrasound transducer array 242. The pressure sensor may be used to measure pressures over a range of 0 to 500 mmHg, or more typically less than 300 mmHg.

In another embodiment of the present invention the IVUS imaging and pressure sensing catheter 100 may be used to image a coronary artery and detect coronary blood pressure. The following details provide an exemplary operation of the four sensor assemblies 210, 220, 230, 240. The sensor control circuitries 214, 244 may include a high voltage signal, an electrical ground, a clock signal, a receiver output signal, and a low voltage signal. The sensor control circuitry 244 may further include a pressure output signal. The high voltage signal may provide a direct current voltage between 5 V and 100V from the console 90 and may be used as a bias voltage for the ultrasound transducer arrays 212, 242. The clock signal may be provided by the console 90, operate between 30 kHz and 150 kHz, and enable coordination of operation of the ultrasound transducer arrays 212, 242 and pressure sensor 246. The low voltage signal may provide a direct current voltage of 3.3 V or 5 V from the console 90 and enable operation of CMOS electronics of the four sensor assemblies 210, 220, 230, 240.

In still another embodiment of the present invention the IVUS imaging and pressure sensing catheter 100 includes ultrasound transducer arrays 212, 242 having an array size of 24×32 elements and operates at a clock rate of 100 kHz.

The ultrasound transducer arrays 212, 242 may be configured to operate as 24 rows of 32 elements. The 100 kHz clock may provide a trigger every 10 µs. In an exemplary imaging sequence 300 transmit and receive operations are performed for each ultrasound transducer array. The time required for this imaging sequence is approximately 3 ms for each ultrasound transducer array, or approximately 12 ms for the four ultrasound transducer arrays of the catheter 100. Following completion of the imaging sequence, the pressure signal from the pressure sensor 246 may be sampled by the console 90. The pressure signal may be sampled between 32 and 256 times to enable averaging of the pressure signals in order to improve signal-to-noise performance. The imaging and sensing sequence can then be repeated. This imaging and pressure sensing sequence enables imaging and sensing rates greater than 60 Hz. It may be appreciated that higher clock rates and alternative imaging and pressure sensing sequences can further increase imaging and sensing rates.

Figure 5:
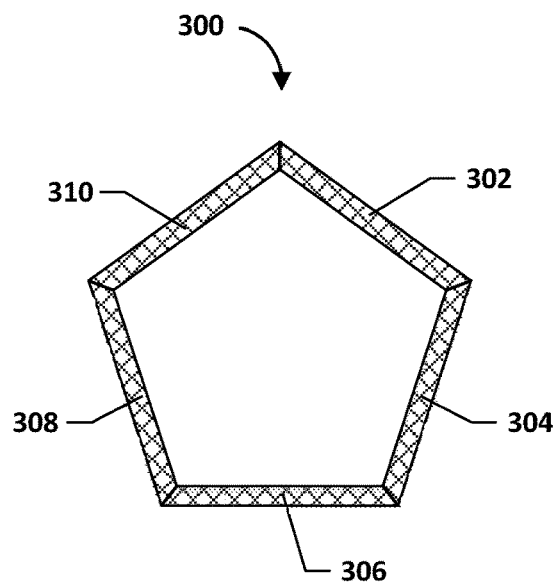
FIG. 5 is a sectional view of an ultrasound imaging array in accordance with an embodiment of the invention.
Figure 6:
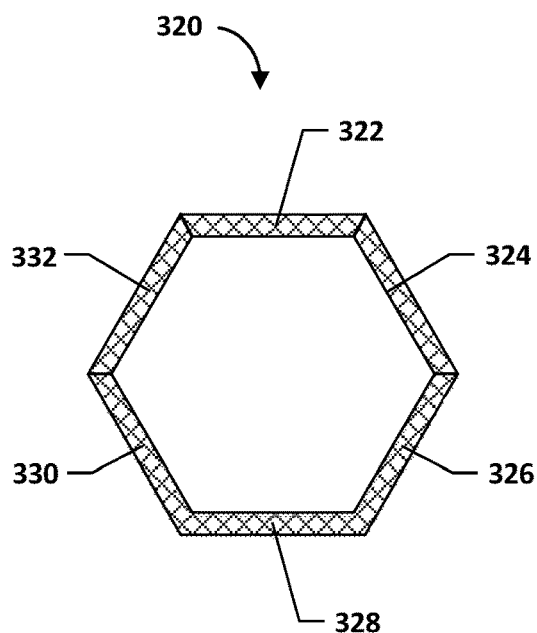
FIG. 6 is a sectional view of an ultrasound imaging array in accordance with an embodiment of the invention.

Referring to FIG. 5, the sensor assembly 300 according to another embodiment of the invention includes a set of five sensor subassemblies 302, 304, 306, 308, 310. Referring to FIG. 6, the sensor assembly 320 according to still another embodiment of the invention includes a set of six sensor subassemblies 322, 324, 326, 328, 330, 332. A potential advantage of additional sensor subassemblies is improved imaging performance, particularly near the transitions between sensor subassemblies. A potential disadvantage of additional sensor subassemblies is increased manufacturing complexity. In another embodiment of the invention the sensor assembly may include less than four sensor subassemblies, such as three sensor subassemblies.

In still yet another embodiment of the invention the sensor subassembly may include piezoelectric materials, such as piezoelectric micromachined ultrasound transducers (PMUTs). PMUTs are a type of micromachined ultrasound transducer that are based on flexural vibrations of a piezoelectric membrane. A potential advantage of PMUTs is that wafer-scale microfabrication techniques may be used to integrate front-end electronics with PMUTs.

Figure 7:
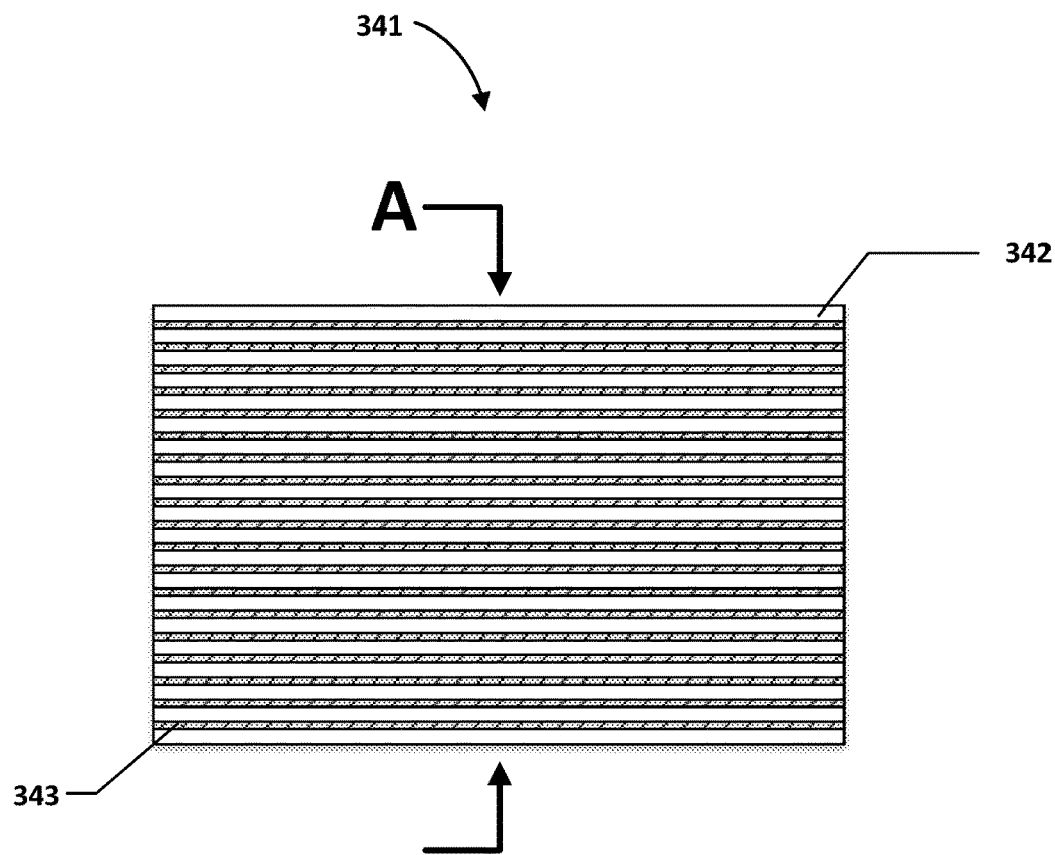
FIG. 7 is a top view of an ultrasound array in accordance with an embodiment of the invention.
Figure 7A:
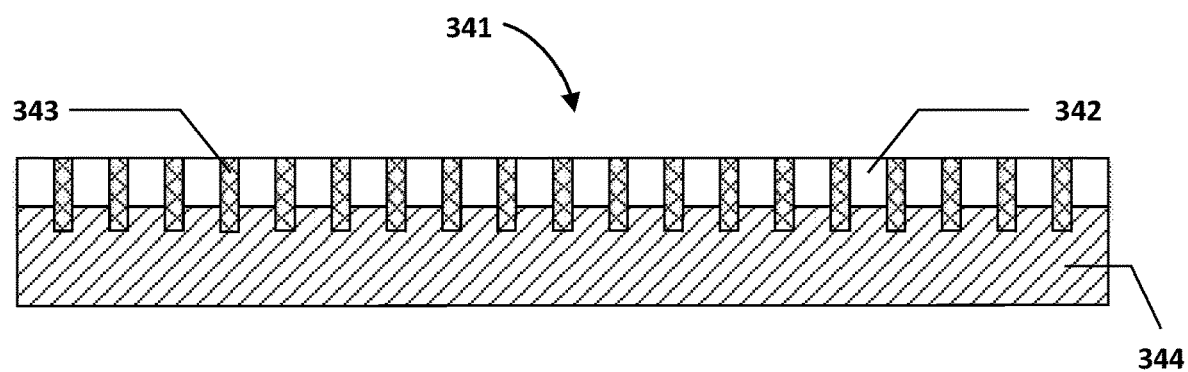
FIG. 7A is a sectional view taken along lines A-A of FIG. 7.
Figure 8:
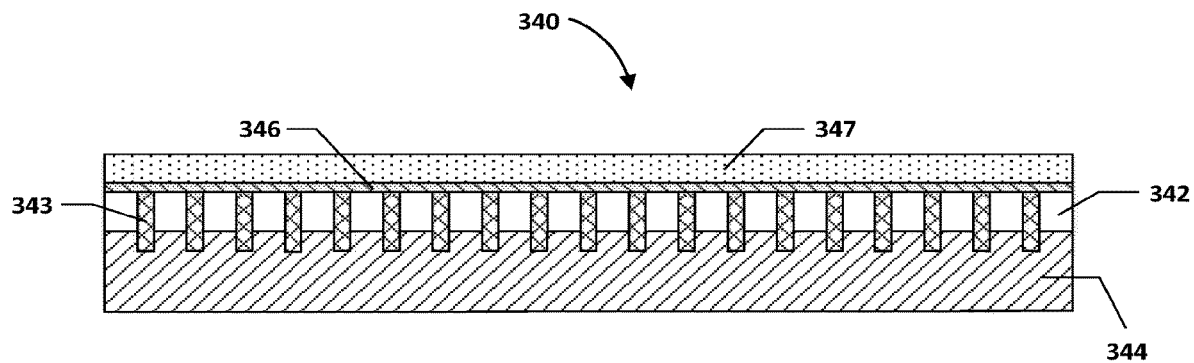
FIG. 8 is a sectional view of an ultrasound imaging array in accordance with an embodiment of the invention.

Referring to FIGS. 7, 7A, and 8, a sensor subassembly 340 according to one embodiment of the invention includes an array of piezoelectric elements 342. A partial acoustic stack 341 includes piezoelectric elements 342, kerfs 343, and backing material 344. Types of piezoelectric material may include lead zirconate titanate (PZT), 1-3 piezocomposite, and single crystal (e.g., PMN-PT, PIN-PMN-PT). The kerf 343 may be filled or unfilled (so-called air kerf). Types of kerf filler materials include epoxies and urethane. The backing material 344 may include one or more layers and may be electrically conductive. Types of backing material include metal-loaded epoxies, epoxy-filled metal foams, and tungsten carbide.

The sensor subassembly 340 may further include a ground electrode 346 and a matching layer 347. The ground electrode 346 enables electrical connectivity to the active piezoelectric material. The ground electrode may be composed of one of more conductive materials such as metals, including gold, chrome, copper, and tungsten. The matching layer 347 may include one or more layers. Types of matching layer materials include glass-ceramics (e.g., Macor®), metal-loaded epoxies, room-temperature vulcanization (RTV) silicone, and urethane.

According to one embodiment of the invention a sensor subassembly may have a 20 MHz transducer array. The dimensions of the array are approximately 0.6 mm by 0.8 mm. The 20 MHz transducer array includes a piezoelectric material layer of PZT having approximately 0.09 mm thickness, a matching layer of silver-loaded epoxy having a thickness of approximately 0.025 mm, and a backing layer of silver- and tungsten-loaded epoxy having a thickness between 0.1 mm and 0.3 mm. The array has 16 elements having a half-wavelength pitch of approximately 0.04 mm. The array kerf width may range between 0.005 mm and 0.03 mm. Narrower kerfs can enable increased transducer sensitivity at a potential cost of increased manufacturing complexity.

Figure 9:
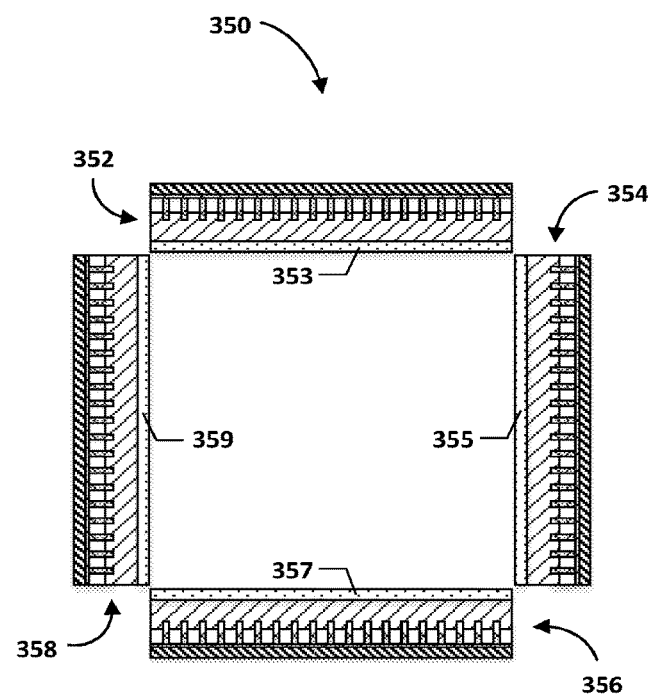
FIG. 9 is a sectional view of an ultrasound imaging array in accordance with an embodiment of the invention.

Referring to FIG. 9, a sectional view piezoelectric sensor assembly 350 according to one embodiment of the invention includes a set of four piezoelectric sensor subassemblies 352, 354, 356, 358. The sensor assembly 350 further includes a flexible circuit assembly made of four flexible circuit arms 353, 355, 357, 359. Each sensor subassembly is electrically connected to one flexible circuit arm. Sensor subassembly 352 and flexible circuit arm 353, sensor subassembly 354 and flexible circuit arm 355, sensor subassembly 356 and flexible circuit arm 357, and sensor subassembly 358 and flexible circuit arm 359 are respectively electrically connected. The piezoelectric sensor assembly 350 may be positioned within the distal tip 110 of the catheter 100, similar to the sensor assembly 200 shown in FIG. 2.

Figure 10:
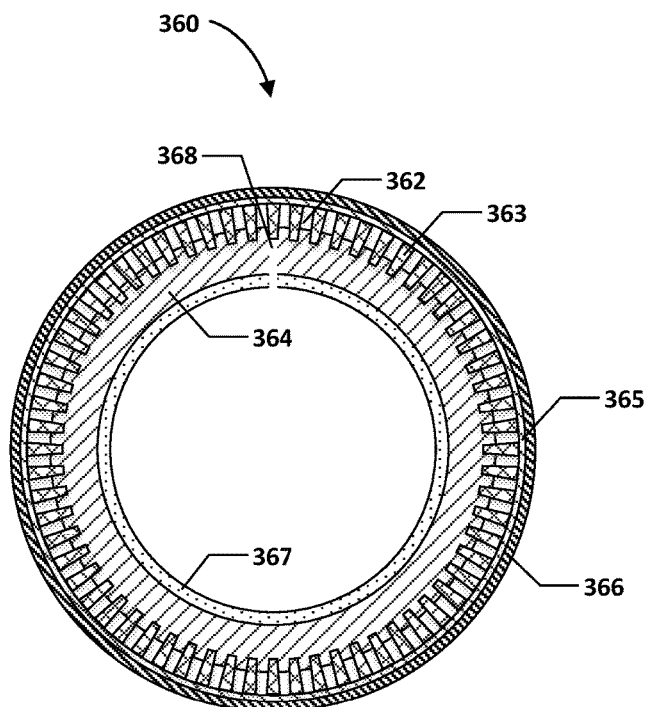
FIG. 10 is a sectional view of an ultrasound imaging array in accordance with an embodiment of the invention.

Referring to FIG. 10, a sectional view of a piezoelectric sensor assembly 360 according to one embodiment of the invention includes a ring array of piezoelectric elements 362, kerfs 363, a backing layer 364, a ground electrode 365, a matching layer 366, and a flexible circuit assembly 367.

The acoustic stack can be manufactured as a linear array, including forming the partial acoustic stack by bonding the piezoelectric material to the backing material, dicing the partial acoustic stack, and then curving the partial acoustic stack to form a ring. After curving, the diced kerfs may be filled with kerf filler material, the ground electrode is added, and the matching layer is added. The kerf widths may taper from the ground electrode side to the backing layer side due to the curving process. The ring array may include a gap 368 between the ends of the array after curving. The piezoelectric sensor assembly 360 may be positioned within the distal tip 110 of the catheter 100, similar to the sensor assembly 200 shown in FIG. 2. Materials and thicknesses of the transducer layers may be similar to the 20 MHz transducer array described above.

Figure 11:
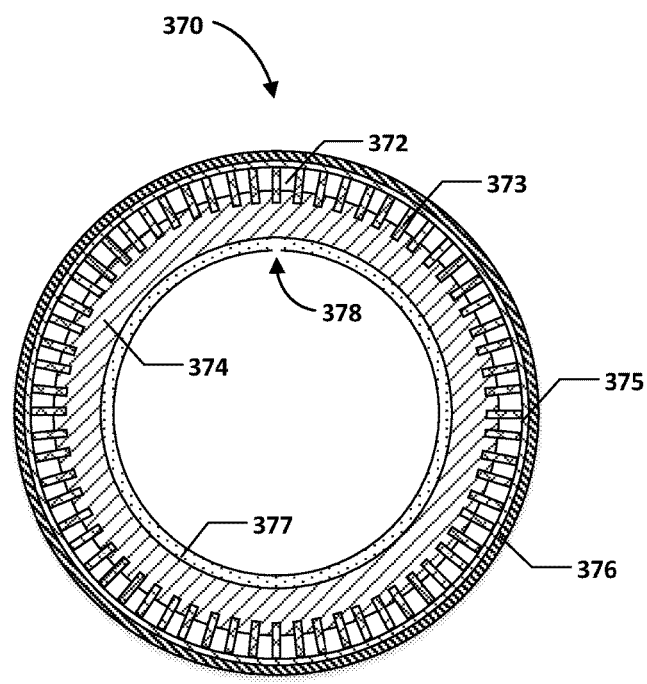
FIG. 11 is a sectional view of an ultrasound imaging array in accordance with an embodiment of the invention.

Referring to FIG. 11, a sectional view of a piezoelectric sensor assembly 370 according to another embodiment of the invention includes a ring array of piezoelectric elements 372, kerfs 373, a backing layer 374, a ground electrode 375, a matching layer 376, and a flexible circuit assembly 377. The piezoelectric material may be a piezoelectric ring having an outer diameter, inner diameter, and length. The piezoelectric ring is bonded to the backing material and then diced. The diced kerfs may be filled with kerf filler material kerfs. The ground electrode and matching layer can then be added. The flexible circuit assembly 377 may include a gap 378 between the edges. The piezoelectric sensor assembly 370 may be positioned within the distal tip 110 of the catheter 100, similar to the sensor assembly 200 shown in FIG. 2. Materials and thicknesses of the transducer layers may be similar to the 20 MHz transducer array described above.

Figure 12:
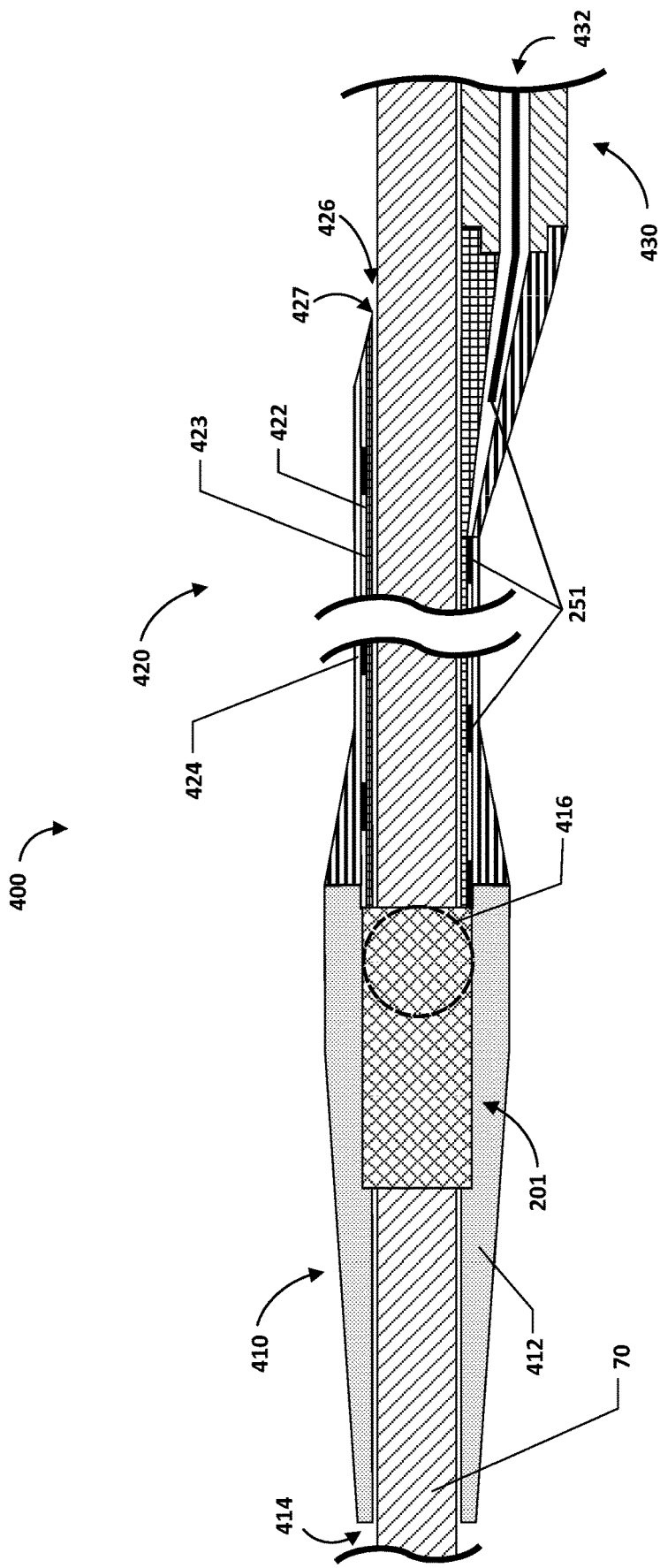
FIG. 12 is a partial sectional view of a catheter in accordance with an embodiment of the invention.

Referring to FIG. 12, a partial sectional view of the distal end of an IVUS imaging and pressure sensing catheter 400 according to one embodiment of the invention is shown. The catheter 400 includes a distal tip 410, a distal shaft 420, a mid-shaft 430, and a sensor assembly 201. The distal tip 410 may include a tapered, elongated tube 412 having at least one layer. The distal tip 410 further includes a guide wire lumen entry port 414 and a side port 416. The distal tip includes a lumen having an inner diameter suitable for a 0.014" guide wire, generally an inner diameter of 0.0165". The distal tip wall thickness may taper from a proximal thickness generally between 0.003" and 0.009" to a distal thickness generally between 0.001" and 0.003". The distal tip has a length generally between 5 mm and 30 mm. Pebax has been found to be a suitable material for the distal tip 410. A distal tip may also include an inner liner made of HDPE or PTFE to reduce friction between the distal tip and a guide wire 70. The side port 416 enables fluid communication between a blood-filled coronary artery and at least a portion of the sensor assembly 201. The sensor assembly 201 includes a flexible circuit assembly 251. A platinum/iridium radiopaque marker band (not shown) may be included in the distal tip to aid visualization of the catheter in x-ray angiographic images.

The distal tip 410 is bonded to the distal shaft 420. The distal shaft 420 can have a proximal end, a distal end, and a length extending between the proximal and distal ends. The distal shaft 420 should have an outer diameter sufficiently small to minimize effects on coronary artery blood flow. The outer diameter of the distal shaft 420 is preferably 0.023" or smaller. The distal shaft 420 has a lumen 426 with an inner diameter suitable for the 0.014" guide wire 70, generally an inner diameter of 0.0165". The distal shaft 420 further includes a guide wire exit port 427. In one embodiment the distal shaft 420 is substantially tubular and includes a three-layered structure, including an inner layer 422, a middle layer 423, and an outer layer 424. The inner layer 422 may be made made of HDPE or PTFE or polyimide to reduce friction between the distal shaft 420 and the guide wire 70. The thickness of the inner layer 422 is generally less than 0.002", preferably 0.001" or smaller. The middle layer 423 includes the flexible circuit assembly 251. The flexible circuit assembly is arranged around the inner layer 422, by wrapping, rolling, or folding. The thickness of the middle layer is generally 0.001". The outer layer 424 includes a biocompatible polymer, such as polyimide or nylon heat shrink tubing, and has a thickness of generally less than 0.002", preferably 0.001" or smaller. The distal shaft 420 generally has a length between 15 cm and 25 cm. This embodiment of the invention provides a long rail engagement with the guide wire 70 that may improve the pushability of the catheter and trackability of the catheter on the guide wire.

The distal shaft 420 is bonded to the mid-shaft 430. The mid-shaft can have a proximal end, a distal end, and a length extending between the proximal and distal ends. The mid-shaft shaft can include any suitable material with sufficient rigidity and torsional stiffness to provide adequate push and torque characteristics along the shaft's length. The mid-shaft may be substantially similar in design to the distal shaft 120 shown in FIG. 2. In some embodiments, the distal shaft includes a hypotube. The hypotube may be a spiral-cut, stainless steel hypotube. In another embodiment the distal shaft includes a PEEK shaft, wherein the PEEK shaft provides rigidity and torsional stiffness to provide push and torque characteristics sufficient for the operator to deliver the device over a guide wire. The distal shaft further includes at least one lumen 432. The mid-shaft shaft may further include a polymer jacket and a polymer liner to seal the lumen 432 from the external blood-filled coronary artery. The outer diameter of the mid-shaft shaft 430 is preferably 0.050" or smaller. The inner diameter of the mid-shaft shaft may be 0.040" or smaller.

Figure 13:
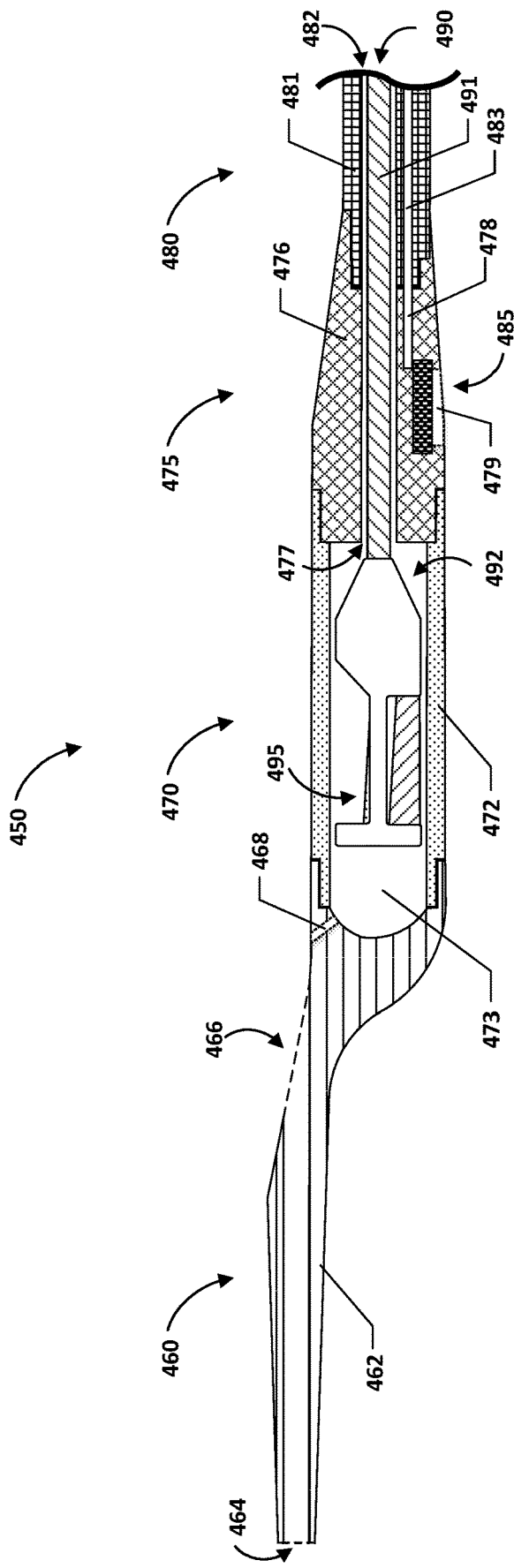
FIG. 13 is a partial sectional view of a catheter in accordance with an embodiment of the invention.

Referring to FIG. 13, a partial sectional view of the distal end of an IVUS imaging and pressure sensing catheter 450 according to another embodiment of the invention is shown. The catheter 450 includes a distal tip 460, an imaging window section 470, a transition section 475, a distal shaft 480, a pressure sensor assembly 485, and an imaging core assembly 490.

The distal tip 460 may include a tapered, elongated tube 462 having at least one layer. The distal tip 460 further includes a guide wire entry port 464 and a guide wire exit port 466. The distal tip has an inner diameter suitable for a 0.014" guide wire, generally an inner diameter of 0.0165". The distal tip wall may taper from a proximal thickness generally between 0.003" and 0.009" to a distal thickness generally between 0.001" and 0.003". The distal tip has a length generally between 5 mm and 30 mm. Pebax has been found to be a suitable material for the distal tip 460. A distal tip may also include an inner liner made of HDPE or PTFE to reduce friction between the distal tip and a guide wire (not shown). A platinum/iridium radiopaque marker band (not shown) may be included in the distal tip to aid visualization of the catheter in x-ray angiographic images.

The distal tip 460 is bonded to the imaging window section 470. The imaging window section 470 can have a proximal end, a distal end, and a length extending between the proximal and distal ends. The outer diameter of the imaging window section 470 is preferably 0.040" (approximately 3 F.) or smaller. The imaging window section wall 472 may have a thickness in the range of 0.001" to 0.005", such as 0.0025". The imaging window section lumen 473 has a diameter that is suitable to house a transducer housing 492. The length of the imaging window section 470 may be between 5 mm and 10 mm. Suitable materials for the imaging window section include HDPE, low-density polyethylene (LDPE), and a blend of HDPE and LDPE. Such materials are known to have relatively low ultrasound attenuation properties that are suitable for ultrasonic imaging.

The imaging window section 470 is bonded to the transition section 475. The transition section 475 can have a proximal end, a distal end, and a length extending between the proximal and distal ends. The transition section 475 may have an outer diameter that varies from a maximum diameter equal to the outer diameter of the imaging window section 470 to a minimum diameter equal to the outer diameter of the distal shaft 480. The transition section 475 may have a first lumen 477 of sufficient size to house a torque coil 491 of the imaging core assembly 490, generally a lumen diameter of approximately 0.023". The transition section 475 may have a second lumen 478 of sufficient size to house an optical fiber or a cable (not shown) for communication with the pressure sensor assembly 485. The pressure sensor may be located within the transition section wall 476. A side port 479 enables fluid communication between a blood-filled coronary artery and the pressure sensor assembly 485. Suitable materials for the transition section 475 include HDPE, LDPE, and a blend of HDPE and LDPE.

The transition section 475 is bonded to the distal shaft 480. The distal shaft 480 should have an outer diameter sufficiently small to minimize effects on coronary artery blood flow. The distal shaft wall 481 may be composed of HDPE, LDPE, and a blend of HDPE and LDPE. The outer diameter of the distal shaft 480 is preferably 0.028" or smaller. The distal shaft 480 has a first lumen 482 of sufficient size to house a torque coil 491 of the imaging core 490, generally a lumen diameter of approximately 0.023". The distal shaft first lumen 482 is coaxial with the transition section first lumen 477. An additional function of the distal shaft first lumen 482 is flushing saline from the proximal end of the catheter to the imaging window section. Saline acts an acoustic couplant that enables the transmission of ultrasound energy from an ultrasound transducer to the exterior of the catheter. The distal shaft first lumen 482 continues through the transition section 475 and provides fluid communication to the imaging window section lumen 473. Flushing the catheter with saline facilitates removal of any air bubbles that may be present in the imaging window section lumen 473. Air bubbles may exit the catheter through a vent 468.

The distal shaft 480 has a second lumen 483 of sufficient size to house an optical fiber or a cable (not shown) for communication with the pressure sensor 485. The distal shaft second lumen 483 is coaxial with the transition section second lumen 478. The distal shaft 480 generally has a length between 15 cm and 25 cm.

The imaging core assembly 490 includes the torque coil 491, the transducer housing 492, and an ultrasound transducer 495. The imaging core further includes a transmission line (not shown) that is housed within the torque coil 491 and transducer housing 492 and provides an electrical connection to the ultrasound transducer 495. The imaging core is capable of transmitting and receiving ultrasound pressure signals while rotating. The ultrasound pressure signals may be processed by the console 90 to form ultrasound images.

Figure 14:
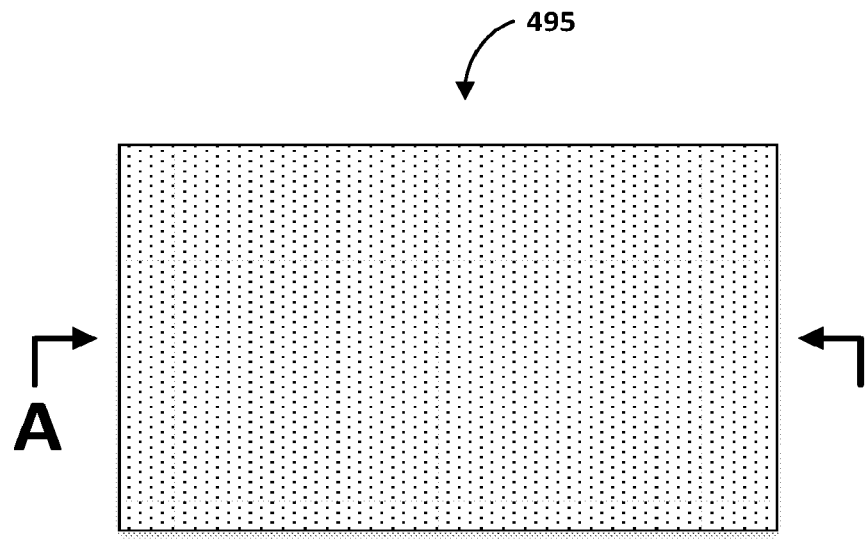
FIG. 14 is a top view of an ultrasound transducer in accordance with an embodiment of the invention.
Figure 14A:
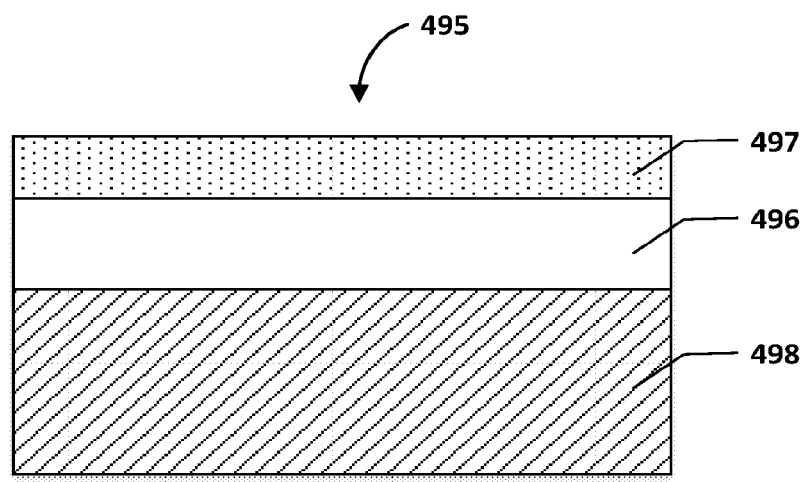
FIG. 14A is a sectional view taken along lines A-A of FIG. 14.

Referring to FIGS. 14 and 14A, the ultrasound transducer 495 according to one embodiment of the invention includes a piezoelectric layer 496, a matching layer 497, and a backing layer 498. The piezoelectric layer 496 may include lead zirconate titanate (PZT), 1-3 piezocomposite, or single crystal (e.g., PMN-PT, PIN-PMN-PT). The matching layer 497 may include one or more layers of materials such as glass-ceramics (e.g., Macor®), metal-loaded epoxies, RTV silicone, and urethane. The backing material 498 may include one or more layers and may be electrically conductive. Types of backing material include metal-loaded epoxies, epoxy-filled metal foams, and tungsten carbide.

According to one embodiment of the invention an ultrasound transducer 495 may operate at a frequency of 60 MHz. The width and length of the transducer as shown in FIG. 12 are respectively approximately 0.6 mm by 0.8 mm. The 60 MHz transducer includes a piezoelectric material layer 496 of PZT having approximately 0.03 mm thickness, a matching layer 497 of silver-loaded epoxy having a thickness of approximately 0.01 mm, and a backing layer of silver- and tungsten-loaded epoxy having a thickness between 0.1 mm and 0.4 mm.

Referring now to FIGS. 15, 15A, and 15B, a partial sectional view of the distal end of an IVUS imaging and pressure sensing catheter 500 according to another embodiment of the invention is shown. The catheter 500 includes a distal tip 460, an imaging section 520, a transition section 530, a distal shaft 540, a pressure sensor assembly 550, and an imaging core assembly 560.

The distal tip 460 is bonded to the imaging window section 520. The imaging window section 520 can have a proximal end, a distal end, and a length extending between the proximal and distal ends. The outer diameter of the imaging window section 520 is preferably 0.046" (approximately 3.5 F.) or smaller. The imaging window section wall 521 may have a thickness in the range of 0.001" to 0.005", such as 0.003". Suitable materials for the imaging window section include HDPE, LDPE, and a blend of HDPE and LDPE. The imaging window section 520 includes a first lumen 522 having a diameter that is suitable for an ultrasound transducer 562 and a rotating acoustic mirror 564. The imaging window section 520 further includes a second lumen 523 having a diameter that is suitable for a transmission line 563. The length of the imaging window section 520 may be between 3 mm and 10 mm. The imaging window section 520 still further includes a bearing section 524 that includes a third lumen 525 that is used for positioning the ultrasound transducer 562 within the imaging window section.

The imaging window section 520 is bonded to the transition section 530. The transition section 530 can have a proximal end, a distal end, and a length extending between the proximal and distal ends. The transition section 530 may have an outer diameter that varies from a maximum diameter equal to the outer diameter of the imaging window section 520 to a minimum diameter equal to the outer diameter of the distal shaft 540.

The transition section 530 may have a first lumen with first diameter 533 of sufficient size to position a micromotor 566 and a second diameter 534 of sufficient size to house electrical cables, including micromotor cables 567. The first diameter 533 of the first lumen may be in the range between 0.020" and 0.040". The second diameter 534 of the first lumen may be in the range between 0.010" and 0.020". The pressure sensor assembly 550 may be located within the transition section wall 532. A side port 536 enables fluid communication between a blood-filled coronary artery and the pressure sensor assembly 550. The transition section 530 may have a second lumen 537 of sufficient size to house an electrical cable 552 for communication with the pressure sensor 550. The transition section 530 may have a third lumen 538 of sufficient size to house the transmission line 563 for electrical coupling to the ultrasound transducer 562. Suitable materials for the transition section 530 include HDPE, LDPE, and a blend of HDPE and LDPE.

The transition section 530 is bonded to the distal shaft 540. The distal shaft 540 should have an outer diameter sufficiently small to minimize effects on coronary artery blood flow. The distal shaft wall 542 may be composed of HDPE, LDPE, and a blend of HDPE and LDPE. The outer diameter of the distal shaft 540 is preferably 0.025" or smaller. The distal shaft 540 has a first lumen 544 of sufficient size to house electrical cables, including the pressure sensor cables 552, the ultrasound transducer transmission line 563, and the micromotor cables 567. The first lumen diameter 544 may be in the range between 0.010" and 0.020". The distal shaft 540 generally has a length between 15 cm and 25 cm.

The distal shaft 540 has flushing lumens 546, 547 for flushing saline from the proximal end of the catheter to the imaging window section. Saline acts an acoustic couplant that enables the transmission of ultrasound energy from the ultrasound transducer 562 to the exterior of the catheter. The flushing lumens 546, 547 continue through the transition section 530 and provide fluid communication to the imaging window section first lumen 522. Additional flushing lumens 526, 527, 528, 529 of the bearing section 524 facilitate removal of any air bubbles that may be present in the imaging window section first lumen 522. Air bubbles may exit the catheter through a vent 468.

The imaging core 560 includes the ultrasound transducer 562, the ultrasound transducer transmission line 563, the acoustic rotating mirror 564, the micromotor 566, and the micromotor electrical cables 567. The rotating acoustic mirror 564 is coupled to the micromotor 566. The imaging core is capable of transmitting ultrasound pressure signals into surrounding tissue and receiving ultrasound pressure signals scattered back from the surrounding tissue. The catheter operates in a side-looking manner wherein the ultrasound transducer 562 transmits ultrasound pressure signals toward the rotating acoustic mirror 564 that in turn reflects the ultrasound pressure signals toward surrounding tissue. The direction of the transmitted ultrasound pressure signals varies with the rotation of the rotating acoustic mirror 564. The received ultrasound pressure signals may be processed by the console 90 to form ultrasound images.

An important aspect of the catheter 500 is an imaging core having a micromotor. The use of a micromotor that is located in the distal end of the catheter eliminates the need for a torque coil in a mechanically rotating imaging catheter. Removal of a torque coil potentially enables designs of distal shafts having a reduced outer diameter. A reduction in outer diameter of the distal shaft may reduce influence on blood flow in a blood vessel.

Referring to FIGS. 1 and 16, a flow diagram 600 illustrates one embodiment of a method to use a pressure sensing and IVUS imaging catheter 100 to guide treatment of a patient 40. Before use of the IVUS imaging and pressure sensing catheter a patient will be positioned on a patient table in a catheter laboratory. A physician will have gained access to the patient's arterial system, delivered a guide catheter to the ostium of a coronary artery of interest, and delivered a guide wire through the guide catheter to the coronary artery of interest. The physician loads the pressure sensing and IVUS imaging catheter onto the guide wire 604 and delivers the catheter to the distal end of the guide catheter 606. The physician equalizes the catheter 608 to insure that the pressure sensing and IVUS imaging catheter detects the same pressure value at the aorta as detected by other aorta pressure reading devices in the catheter laboratory. After equalization the physician crosses the coronary artery lesion of interest 610. The physician then induces hyperemia 612, typically by administration of a pharmaceutical agent such as adenosine. The catheter 100 and console 90 are used to measure pressure distal to the lesion 614 and then calculate a fractional flow reserve (FFR) value 616. Calculating the FFR value generally includes use of an aortic pressure value that may be provided by additional physiological monitoring equipment that is connected to the patient.

If the FFR value is not less than or equal to 0.80 618 then the physician generally decides to defer treatment of the lesion. The physician withdraws the pressure sensing and IVUS imaging catheter 620 and ends the procedure 650.

If on the other hand the FFR value is less than or equal to 0.80 618, the physician then often treats the lesion by stenting. The physician may use the catheter to image the lesion and vessel in order to determine the vessel size 622 as well as suitable landing spots for placement of a coronary stent. A stent size and length can then be selected 624 based on respectively the vessel size and location of stent landing spots.

An important aspect of the invention is that the pressure sensing and IVUS imaging catheter enables the physician to first determine whether a lesion should be treated based on a FFR measurement and secondly select stent size and length based on IVUS imaging. A further important aspect of the invention is that the FFR measurement and IVUS imaging are performed without having to exchange devices or change the position of the guide wire.

After selection of the stent size, the physician withdraws the pressure sensing and IVUS imaging catheter 626. The physician will then stent the lesion 628. Stenting may include loading a stent catheter onto the guide wire, delivering the stent catheter to the lesion, deploying the stent, and then removing the stent catheter. To determine if the stent is optimally deployed, the physician can perform IVUS imaging or FFR measurement or both IVUS imaging and FFR measurement. The physician reloads the pressure sensing and IVUS imaging catheter onto the guide wire 630 and delivers the catheter to the stented lesion 632. The physician uses the catheter 100 and console 90 to image the stented lesion 634 and calculate the cross-sectional area of the stent 636. To calculate post-stent FFR, the physician induces hyperemia 638, typically by administration of a pharmaceutical agent such as adenosine. The catheter 100 and console 90 are used to measure pressure 640. The pressure may be measured at multiple locations including distal to the stent and proximal to the stent. The pressure may be further measured during a pullback of the catheter through the stent. The physician can then calculate a post-stent FFR value 642.

An important aspect of the invention is that the pressure sensing and IVUS imaging catheter enables the physician to measure stent cross-sectional area and post-stent FFR value without having to exchange devices or change the position of the guide wire.

After calculation of stent cross-sectional area and post-stent FFR value the catheter can be removed from the patient 644. If the stent cross-sectional area and post-stent FFR value are not optimal 646, the physician can further expand the stent cross-sectional area by post-dilating with a balloon catheter 648. For example, the stent cross-sectional area may be considered not optimal if it is less than a target cross-sectional area, such as less than 90% of the cross-sectional area of the blood vessel distal to the lesion. Further, a post-stent FFR value can be considered not optimal if it is less than a target post-stent FFR value, such as 0.95 or 0.90. If the stent cross-sectional area and FFR value are optimal, the physician can end the procedure 650.

According to other embodiments of the invention the pressure sensing and IVUS imaging catheter may be used to calculate other coronary physiology indices, such as instantaneous wave-free ratio or resting (non-hyperemic) pressure gradients. A potential advantage of such methods is that to simplify patient workflow and reduce patient discomfort by eliminating need for maximal hyperemia, which is required for FFR calculations.

While particular embodiments of the present invention have been shown and described, modifications may be made, and it is therefore intended to cover all such changes and modifications which fall within the true spirit and scope of the invention as defined by those claims.

What is claimed is:

1. A sensing catheter for insertion into a blood vessel, the sensing catheter comprising:
   a first portion including:
      a first lumen extending between an entry port and an exit port, the first lumen structured for receiving a guide wire having an outer diameter of 0.014 inches; and
      a sensor assembly surrounding the first lumen, the sensor assembly including:
         at least one ultrasound transducer array; and
         a pressure sensor; and
   a second portion extending from the first portion, the second portion including:
      a second lumen for housing a flexible circuit assembly connected to the sensor assembly, wherein the second portion has an outer diameter less than an outer diameter of the first portion, and wherein the outer diameter of the second portion when combined with an unenclosed portion of the guide wire is less than a threshold determined by an artery lumen cross-sectional area and an estimated percentage of occlusion.

2. The sensing catheter of claim 1, wherein the pressure sensor and the at least one ultrasound transducer array are fabricated on a same substrate.

3. The sensing catheter of claim 1, wherein the sensor assembly includes a set of sensor subassemblies positioned around the first lumen, and the flexible circuit assembly further includes flexible circuit arms each connected to a sensor subassembly of the set of sensor subassemblies.

4. The sensing catheter of claim 1, wherein the at least one ultrasound transducer array has a width between 0.012 inches and 0.024 inches, and a length between 0.020 inches and 0.8 inches.

5. The sensing catheter of claim 1, wherein the sensor assembly includes a ring array of piezoelectric elements.

6. The sensing catheter of claim 1, wherein the first lumen has an inner diameter of 0.0165 inches extending between the entry port and the exit port.

7. The sensing catheter of claim 1, wherein the first portion is tapered.

8. The sensing catheter of claim 1, wherein the first portion has a first wall thickness between 0.003 inches and 0.009 inches at the exit port and a second wall thickness between 0.001 inches and 0.003 inches at the entry port.

9. The sensing catheter of claim 1, wherein the first portion has a length between 0.20 inches and 1.18 inches for tracking along the guide wire.

10. The sensing catheter of claim 1, wherein the first lumen includes an inner liner that reduces friction between the first lumen and the guide wire.

11. The sensing catheter of claim 1, wherein the first portion is made of an elastomer.

12. The sensing catheter of claim 1, wherein the first portion includes a side port for fluid communication between a coronary artery and a portion of the sensor assembly.

13. The sensing catheter of claim 1, wherein the second portion includes a jacket for sealing the flexible circuit assembly inside the second lumen.

14. The sensing catheter of claim 1, wherein the second lumen has an inner diameter of 0.016 inches or less.

15. The sensing catheter of claim 1, wherein the first lumen is discontinued along a length of the second portion.

16. The sensing catheter of claim 1, wherein the second portion includes a hypotube.

* * * * *